(12) United States Patent
De Vries et al.

(10) Patent No.: US 11,477,584 B2
(45) Date of Patent: Oct. 18, 2022

(54) HEARING SYSTEM, ACCESSORY DEVICE AND RELATED METHOD FOR SITUATED DESIGN OF HEARING ALGORITHMS

(71) Applicant: GN HEARING A/S, Ballerup (DK)

(72) Inventors: Aalbert De Vries, Eindhoven (NL); Joris Kraak, Eindhoven (DK); Andrew Dittberner, Antioch, IL (US)

(73) Assignee: GN HEARING A/S, Ballerup (DK)

( * ) Notice: Subject to any disclaimer, the term of this patent is extended or adjusted under 35 U.S.C. 154(b) by 397 days.

(21) Appl. No.: 16/601,107

(22) Filed: Oct. 14, 2019

(65) Prior Publication Data

US 2020/0145765 A1 May 7, 2020

(30) Foreign Application Priority Data

Nov. 5, 2018 (EP) .................................... 18204394

(51) Int. Cl.
*H04R 25/00* (2006.01)
*G06F 9/4401* (2018.01)
*G06N 7/00* (2006.01)
*G06N 20/00* (2019.01)

(52) U.S. Cl.
CPC ......... *H04R 25/507* (2013.01); *G06F 9/4401* (2013.01); *G06N 7/005* (2013.01); *H04R 25/70* (2013.01); *G06N 20/00* (2019.01)

(58) Field of Classification Search
CPC .. H04R 25/70; H04R 25/507; H04R 2225/41; H04R 25/50; H04R 25/30; H04R 25/00; H04R 2225/03; H04R 25/305; H04R 5/033; H04R 29/00; H04R 2225/83; H04R 2225/81; G06F 9/4401; G06N 7/005; G06N 20/00

USPC ..... 381/312, 317, 58, 314, 74, 56, 103, 107, 381/71.11, 101, 303
See application file for complete search history.

(56) References Cited

U.S. PATENT DOCUMENTS 9,084,066 B2 * 7/2015 De Vries ................ H04R 25/70
2010/0303269 A1 * 12/2010 Baechler ............... H04R 25/70
381/321

FOREIGN PATENT DOCUMENTS

EP     3 267 695 A1    1/2018
WO   WO 2008/141672 A1   11/2008

OTHER PUBLICATIONS

Extended European Search Report dated Mar. 15, 2019 for corresponding European Application No. 18204394.3.

* cited by examiner

*Primary Examiner* — Norman Yu
(74) *Attorney, Agent, or Firm* — Vista IP Law Group, LLP

(57) ABSTRACT

Hearing system, accessory device, agent and method for situated design of a hearing algorithm of a hearing device is disclosed, the method comprising initializing a model comprising a parameterized objective function; providing one or more operating parameters indicative of the hearing algorithm to the hearing device; obtaining operating data comprising corresponding input data and output data of the hearing device; obtaining evaluation data indicative of user evaluation of the output data; determining one or more updated operating parameters based on the model, the operating data and the evaluation data; and providing the updated operating parameters to the hearing device.

30 Claims, 3 Drawing Sheets

HEARING SYSTEM, ACCESSORY DEVICE AND RELATED METHOD FOR SITUATED DESIGN OF HEARING ALGORITHMS

RELATED APPLICATION DATA

This application claims priority to, and the benefit of, European Patent Application No. 18204394.3 filed on Nov. 5, 2018. The entire disclosure of the above application is expressly incorporated by reference herein.

FIELD

The present disclosure relates to a hearing system, accessory device and related method, in particular a method for situated design of a hearing algorithm of a hearing device.

BACKGROUND

Today's hearing algorithm design methods have inherent limitations. While hearing device users tend to be quite happy when they leave the dispenser's clinic with their new hearing devices, some experience frustrations afterwards due to the incapacity to adapt (personalize) their hearing devices as unforeseen problems occur in-the-field. For instance, the amplified sharp sounds of utensils on a plate may spoil a nice dinner at a restaurant.

SUMMARY

Accordingly, there is a need for improved methods for design of hearing algorithms.

Accordingly, the present disclosure provides a hearing system comprising an accessory device and a hearing device, an accessory device, and method for situated design of a hearing algorithm of a hearing device.

A method for situated design of a hearing algorithm of a hearing device is disclosed, the method comprising initializing a model comprising a parameterized objective function; providing one or more operating parameters indicative of the hearing algorithm to the hearing device; obtaining operating data comprising corresponding input data and output data of the hearing device; obtaining evaluation data indicative of user evaluation of the output data; determining one or more updated operating parameters based on the model, the operating data and the evaluation data; and providing the updated operating parameters to the hearing device.

Further, an accessory device for a hearing system is disclosed, the accessory device comprising a memory module, a processor module, and a wireless interface, wherein the accessory device is configured to perform any of the methods as disclosed herein.

Also disclosed is a hearing system comprising a hearing device and an accessory device as disclosed herein.

It is an important advantage of the present disclosure that a hearing algorithm is continuously updated (in real-time or close to real-time) during normal use of the hearing device.

The present disclosure allows for an improved listening experience to a hearing device user. Further, an effective and convenient way to configure one or more hearing device parameters of a hearing device is provided. For example, situated hearing algorithm design may save one or more time-consuming revisits to the dispenser of the hearing device.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
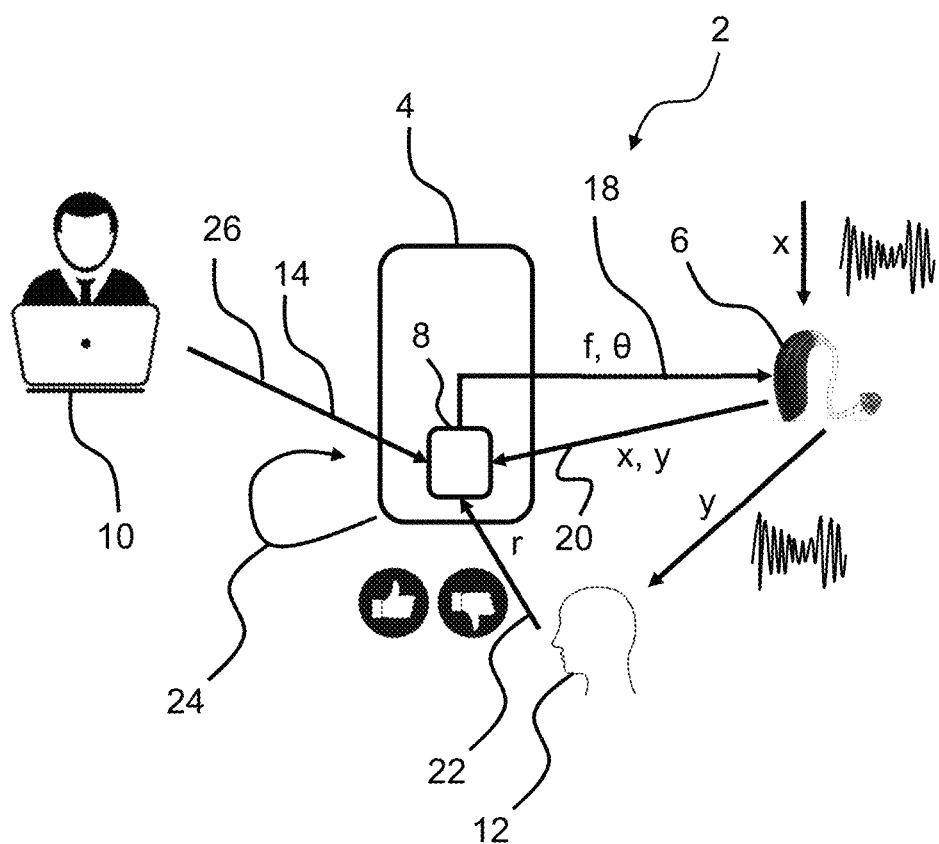
FIG. 1 schematically illustrates an exemplary hearing system with situated design of a hearing algorithm.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

In a situated design process, the problem and solution are developed simultaneously through in-situ experimentation with the environment. The present disclosure proposes to provide the currently best solution proposal, until it fails, and through smart in-situ experimentation with the environment via the agent/accessory device, the problem statement is further developed, which in turn enables improvement of the solution proposals. Situated learning requires that complete design cycles are performed in real-time or close to real-time. In the present disclosure, this experimental process can be executed by an agent, which is represented by a smartwatch- (or smartphone-) resident software program or application that is able to communicate with the hearing device by a communication link, such as a low-energy Bluetooth link, see also FIG. 1.

The present disclosure relates to a method for situated design of a hearing algorithm of a hearing device, wherein the method comprises initializing a model. The model may comprise a parameterized objective function. In one or more exemplary methods, the model is a generative probabilistic model. The model may be a hierarchical Bayesian dynamical system.

The method comprises providing one or more operating parameters indicative of the hearing algorithm to the hearing device. In one or more exemplary methods/systems, the one or more operating parameters may comprise a hearing algorithm identifier and/or a set of hearing device parameters. The set of hearing device parameters may include and/or be indicative of filter coefficients and/or values thereof. The set of hearing device parameters may include and/or be indicative of noise cancellation parameters and/or values thereof. The set of hearing device parameters may include and/or be indicative of compressor gains and/or values thereof. The hearing algorithm identifier may include and/or be indicative of a hearing algorithm selected from a plurality of hearing algorithms.

The method comprises obtaining, e.g. in the accessory device, operating data comprising corresponding input data and output data of the hearing device, e.g. by receiving the input data and/or the output data from the hearing device and/or an intermediate relay device. The method may comprise obtaining, e.g. in the accessory device, operating data comprising corresponding input data and output data of the hearing device by receiving the input data from the hearing device and determine the output data by applying the current hearing algorithm in the accessory device. Accordingly, the accessory device may derive the output data based on the input data, thereby saving transmission power in the hearing device.

The method comprises obtaining, e.g. in the accessory device, evaluation data r indicative of user evaluation of the output data. The evaluation data are aligned with the input data and output data, e.g. providing data tuple(s) comprising corresponding input data, output data, and evaluation data.

The method comprises determining one or more updated operating parameters based on the model, the operating data and the evaluation data followed by providing the updated operating parameters to the hearing device. In other words, operating parameters of the hearing device are adapted in accordance with input data, output data, and evaluation data, in turn providing situated hearing algorithm design, i.e. the operating parameters of the hearing device are advantageously adapted based on user evaluations during normal use of the hearing device.

The method comprises providing the updated operating parameters to the hearing device. In one or more exemplary methods, providing one or more operating parameters to the hearing device comprises providing a hearing algorithm identifier to the hearing device, e.g. by wireless transmission of the hearing algorithm identifier to the hearing device. Thereby the agent is able to select a suitable or optimum hearing algorithm, e.g. from a plurality of hearing algorithms including a first hearing algorithm and a second hearing algorithm. In one or more exemplary methods, providing one or more operating parameters to the hearing device comprises providing one or more hearing device parameters to the hearing device, e.g. by wireless transmission of a set of hearing device parameters to the hearing device.

In one or more exemplary methods, the generative probabilistic model is a generative probabilistic model m given by p(x, y, r, $f$, θ, z|m), where x is input data of the hearing device, y is output data of the hearing device, r is evaluation data, $f$ is a hearing algorithm, θ is hearing device parameters, and z is latent variables.

In one or more exemplary methods, the hearing algorithm is a dynamical system given by $s_{t+1} = f(s_t, x_t, θ)$ $y_t = g(s_t)$ where t is the time index; $x_t$ is input data, $s_t$ is a state vector, $y_t$ is output data which is a fixed function g(·) of the states $s_t$, $f$(·) denotes the hearing algorithm and θ comprises a set of hearing device parameters.

Determining one or more updated operating parameters may comprise solving a probabilistic inference problem given one or more constraints, e.g. a first constraint and/or a second constraint.

In one or more exemplary methods, determining one or more updated operating parameters comprises solving a probabilistic inference problem given by p($f$, θ, |$d_{\leq t}$={(x, y, r)$_{\leq t}$}, r$_{>t}$>0, m), where $f$ is a hearing algorithm, θ is hearing device parameters, $d_{\leq t}$={(x, y, r)$_{\leq t}$} is a first constraint respecting past observations, and r$_{>t}$>0 is a second constraint that future evaluation data should be indicative of a positive user evaluation of the output data.

In one or more exemplary methods, solving the probabilistic inference problem comprises implementing message passing, e.g. on a factor graph realization of the model. The factor graph realization may be a Forney-style Factor graph realization of the model.

In one or more exemplary methods, determining one or more updated operating parameters based on the model, the operating data and the evaluation data comprises minimizing a function, wherein the function is a divergence function, such as an alpha-divergence function.

In one or more exemplary methods, the alpha-divergence function is a function F given by:

$$F[q] = \sum_z q(z) \log \frac{q(z)}{p(d, z)}$$

where the function F is a function of the variational distribution q(z) and d are data tuples (x, y, r). The function $F_{[q]}$ is called the Variational Free Energy (VFE) functional. The VFE is a distance measure between the probability distributions p and q (see formula). The VFE is an example of a larger class of distance measures (between probability distributions) called alpha-divergence. When the VFE is used as distance measure, then probabilistic inference in a factor graph leads to the "Variational Message Passing" (VMP) algorithm. The VFE and VMP algorithm are examples of how to do inference. Other measures/methods for inference based on minimizing the alpha-divergence may be employed, for instance, expectation propagation and belief propagation.

In one or more exemplary methods, the model comprises a first model and a second model. In one or more exemplary methods, the first model is a generative probabilistic model for the input data and the output data and the second model is a generative probabilistic model for the evaluation data. In one or more exemplary methods, the first model is based on an output of the second model, e.g. $u_t^{(1)}$ and $u_t^{(2)}$ in FIG. 3. For example, the output of the second model may modulate or adapt one or more precision parameters in the first model for the hearing device. In other words, the first model and the second model are coupled models.

Further, an accessory device for a hearing system is provided. The accessory device comprises a memory module, a processor module, and a wireless interface. In one or more exemplary methods, the accessory device is configured to perform any of the methods disclosed herein. Further, an agent is disclosed, wherein the agent is configured to perform any of the methods disclosed herein. The agent may be a software module, e.g. an application, that can be installed in the memory module of an accessory device.

Further, a hearing system comprising a hearing device and an accessory device is disclosed.

Additionally, a hearing device is disclosed. The hearing device may be a hearable or a hearing aid, wherein the processor is configured to compensate for a hearing loss of a user.

The hearing device may be of the behind-the-ear (BTE) type, in-the-ear (ITE) type, in-the-canal (ITC) type, receiver-in-canal (RIC) type or receiver-in-the-ear (RITE) type. The hearing aid may be a binaural hearing aid.

The hearing device is configured for wireless communication with one or more devices, such as with another hearing device, e.g. as part of a binaural hearing system, and/or with one or more accessory devices, such as a smartphone and/or a smart watch. The hearing device optionally comprises an antenna for converting one or more wireless input signals, e.g. a first wireless input signal and/or a second wireless input signal, to antenna output signal(s). The wireless input signal(s) may origin from external source(s), such as spouse microphone device(s), wireless TV audio transmitter, and/or a distributed microphone array associated with a wireless transmitter. The wireless input signal(s) may origin from another hearing device, e.g. as part of a binaural hearing system, and/or from one or more accessory devices.

The hearing device comprises a processor for processing input signals, e.g. according to a hearing algorithm, e.g. in order to compensate for hearing loss of a user of the hearing device. The processor provides an electrical output signal based on the input signals to the processor.

The hearing device is configured for receiving one or more operating parameters indicative of the hearing algorithm to the hearing device, and processing input signal according to the one or more operating parameters for provision of an output signal. The output signal is converted to an audio output signal via a receiver. The audio output signal is output to the user. The hearing device is configured to wirelessly transmit the input signal (or one or more parameters or data representative thereof) to the accessory device/agent. In one or more exemplary hearing devices, the hearing device is configured to wirelessly transmit the output signal (or one or more parameters or data representative thereof) to the accessory device/agent. In one or more exemplary hearing devices, a user evaluates the output signal/hearing algorithm by providing user feedback via a button or other input interface, e.g. a motion sensor, on the hearing device. Hence, the hearing device may be configured to determine and/or transmit evaluation data indicative of user evaluation of the output data/hearing algorithm to the accessory device/agent. The hearing device is configured for receiving updated operating parameters indicative of the hearing algorithm to the hearing device, and processing input signal according to the updated operating parameters for provision of an output signal.

FIG. 1 shows an exemplary hearing system illustrating situated design of a hearing algorithm according to the present disclosure. The hearing system 2 comprises an accessory device 4, illustrated here as a smartphone, and a hearing device 6. The accessory device 4 is configured for wireless communication with the hearing device 6, e.g. via a Bluetooth® protocol or other wireless protocol, and comprises or have installed thereon an agent/application 8. Further, the accessory device 4 is configured for wireless communication with a server device or other external device 10, e.g. for download of the agent/application 8 and/or specific settings for the agent/application. A user 12 of the hearing device 6 provides user feedback on the operation/ performance of the hearing device 6 to the agent 8 via interface of the accessory device 4. In the hearing system 2, a model, such as a generative probabilistic model comprising a parameterized objective function is initialized in the agent 8, e.g. by retrieving the model from memory and/or received 14 from external device 10. The model may be a model m given by $p(x, y, r, f, \theta, z|m)$, where x is input data of the hearing device, y is output data of the hearing device, r is evaluation data, f is a hearing algorithm identifier, $\theta$ is hearing device parameters, and z is latent variables.

Consider the agent-based hearing device design scenario of FIG. 1 and assume that a hearing aid algorithm is a dynamical system given by $$s_{t+1} = f(s_t, x_t, \theta)$$

$$y_t = g(s_t)$$

where t is the time index; $x_t$ is input data, $s_t$ is a state vector, $y_t$ is output data which is a fixed function $g(\cdot)$ of the states $s_t$, $f(\cdot)$ denotes the hearing algorithm (the equations) and $\theta$ comprises a set of hearing device parameters or tuning parameters.

The hearing algorithm design comprises three tasks:
1. (algorithm design task). Specify a signal processing algorithm $f(\cdot)$.
2. (fitting task). Assign values to the hearing device parameters $\theta$.
3. (performance evaluation task). Evaluate the performance of the selected values for $f(\cdot)$ and $\theta$.

The agent 8 observes its environment through data tuples $D=\{d_t=(x, y, r)_t; t=1, \ldots, \infty\}$. Thus, the agent obtains operating data comprising corresponding input data x and output data y of the hearing device together with evaluation data r indicative of user evaluation of the output data. Basically, this means that the agent 8 observes current hearing device input and output data $(x_t, y_t)$ and user evaluations (responses) $r_t$ on that input and output data.

In one or more exemplary systems/methods, the agent 8 obtains operating data comprising corresponding input data x and output data y of the hearing device by receiving only the input data x from the hearing device and then determining or calculating the corresponding output data y based on the agent's knowledge on the hearing algorithm performed by the hearing device. In one or more exemplary systems/ methods, the agent 8 obtains operating data comprising corresponding input data x and output data y of the hearing device by receiving both the input data x and the output data y from the hearing device.

User evaluations or responses may include button presses (e.g., like, dislike), gestures, or physiological measurements like heart rate or EEG signals. In one or more exemplary systems/methods, the evaluation data may be obtained via an interface (e.g. one or more buttons) of the hearing device and/or via a graphical user interface of the accessory device. In one or more exemplary systems/methods, the evaluation data may be obtained via a voice recognition module of an accessory device interface.

In one or more exemplary systems/methods illustrated herein, $r_t=0$ indicates a neutral or missing (unobserved) performance appraisals, $r_t>0$ relates to positive evaluations and $r_t<0$ corresponds to unsatisfactory hearing device behavior. In other words, a good evaluation from the user corresponds to a positive value of r, e.g. r=1, a neutral evaluation from the user corresponds to r=0 and a negative evaluation from the user corresponds to a negative value of r, e.g. r=−1.

Furthermore, the agent 8 provides updated operating parameters f, $\theta$ to the hearing device 6. In other words, the agent 8 is capable to push actions $A=\{a_t=(f, \theta)_t; t=1, \ldots, \infty\}$ to the hearing device 6. In this case, actions A include proposals or instructions for the signal processing algorithm $f(\cdot)$ as well as hearing device parameter settings $\theta$. The agent 8 should make the most interesting proposals $a_t$ (from the end user's perspective) in as few interactions (evaluations) as possible.

The method for situated design of a hearing algorithm comprises an in-situ executed and optionally repeating loop of four steps or tasks. A loop comprises the following tasks:

TRY 18 comprising the act of providing operating parameters to the hearing device;

EXECUTE 20 comprising the act of obtaining operating data (input data and/or output data) from the hearing device;

EVALUATE 22 comprising the act of obtaining evaluation data indicative of user evaluation of the output data; and ADAPT 24 comprising the act of determining one or more updated operating parameters based on the model, the operating data and the evaluation data.

The method is seeded or initialized by pushing 26 a model to the agent (also denoted the ASSUME task). Exemplary design phases are described in further detail below.

The Assume Task (Ref 26)

A fully probabilistic modeling approach is taken. This approach starts with the specification of a generative model $$p(x, y, r, f, \theta, z|m) \tag{1}$$

where m identifies the agent. We use variables-without-subscripts like $x \equiv (x_1, x_2, \ldots)$ to indicate sequences (and similar for the other variables). A generative model is a probabilistic joint model for all variables in the system-under-study. The agent's model consists of sensory/observed input signals (data tuples) $d=(x, y, r)$, actions $a=(f, \theta)$, and internal (hidden, latent, unobserved) variables z. Here, we will call this the ASSUME step, which reflects the assumption that model m is true. In a hearing device signal processing context, it is proposed that the model is a hierarchical Bayesian dynamical system, see FIG. 1. Further details of the structure of the model will be described in further detail below.

The Try Task (Ref 18)

Given the generative model is true, the agent is configured to make actions subject to the following constraints:

1. We want to respect all past observations on user preferences, i.e., we want to respect the observations $d_{<t} = \{(x, y, r)_{<t}\}$.

2. We want future user feedback to be positive (since we want users to be happy in the future), i.e., we want $r_{>t} > 0$.

This is the TRY task, which can be stated as a probabilistic inference problem:

$$p(f, \theta | d_{<t} = \{(x, y, r)_{<t}\}, r_{>t} > 0, m) \tag{2}$$

Equation 2 states that the computation of interesting algorithm and parameter setting proposals are treated as an inference problem. In particular, the posterior distribution over $(f, \theta)$ subject to constraints (1) and (2) is computed. This Bayesian inference task (2) is in general intractable, however a way to compute an approximate solution to equation (2) is described below.

The Execute Task (Ref 20)

This task comprises execution of the hearing algorithm as specified by equation (3), which is implemented at the hearing device. The hearing algorithm is a dynamical system given by $$s_{t+1} = f(s_t, x_t, \theta) \tag{3}$$

$$y_t = g(s_t)$$

where t is the time index; $x_t$ is input data, $s_t$ is a state vector, $y_t$ is output data which is a fixed function $g(\cdot)$ of the states $s_t$, $f(\cdot)$ denotes the hearing algorithm and $\theta$ comprises a set of hearing device parameters.

The Evaluate Task (Ref 22)

At any time, the hearing device user can critique/evaluate the current behavior (hearing algorithm/output signal) of the hearing device 6 by submitting a 'response' signal $r_t$. This response signal could be a button press on the accessory device 4 or on a secondary accessory device forwarding evaluation data to the agent 8 to indicate that the user is not happy with the current performance of the hearing aid. In one or more exemplary methods/systems, the evaluation data may comprise physiological data of the user, such as heart rate and/or EEG signal.

Accordingly, the agent 8 obtains a signal (evaluation data) that correlates to the performance of the currently active algorithm. As discussed, it is assumed that the agent also is supplied with the current input data and optionally output data indicative of the behavior of the hearing device. The agent may determine the output data based on the input data, thus reducing power consumption in the hearing device. In other words, the agent observes data tuples $d_t = (x_t, y_t, r_t)$. The audio signals are usually sampled at data rates of about 20K samples/second. For most user interfaces, the response signals are sampled at a much lower rate. In that case, it is assumed that $r_t$ is upsampled in an appropriate way to the sampling rate of the audio signals. For instance, in case of a like/dislike button, the following values may be assigned to r:

$$r_t = \begin{cases} 1 & \text{if user presses "like"} \\ -1 & \text{if user presses "dislike"} \\ 0 & \text{otherwise (missing values)} \end{cases} \tag{4}$$

The Adapt Task (Ref 24)

In this step, the model of the agent 8 absorbs the observations:

i.

$$p(x, y, r, f, \theta, z|m) \propto p(x, y, r, f, \theta, z|m) \cdot \delta(d_t - \hat{d}_t) \cdot p(r_{>t} > 0) \tag{5}$$

In equation (5), the observed values $\hat{d}_t = (\hat{x}_t, \hat{y}_t, \hat{r}_t)$ are assigned to the model variables $d_t = (x_t, y_t, r_t)$ and any (counterfactual) future observations of the user responses are constrained to be positively valued. This is optionally followed by re-normalization of the probability distribution. The effect of this substitution is that any subsequent (Bayesian) reasoning with the model will take all (factual and counterfactual) observations into account (this is constraint 1 and 2 as described in the TRY step).

The acts TRY-EXECUTE-EVALUATE-ADAPT may be repeated for all time steps.

The acts TRY-EXECUTE-EVALUATE-ADAPT may be repeated at a certain frequency, e.g. once every 1 minute, once every 5 minutes, once every 10 minutes or once every 15 minutes. In one or more exemplary methods/system, the acts TRY-EXECUTE-EVALUATE-ADAPT may be triggered by a user evaluation and/or stopped in response to a user input. In one or more exemplary methods/system, the acts TRY-EXECUTE-EVALUATE-ADAPT cycle may be executed when $r \neq 0$, i.e., whenever there is a relevant appraisal/feedback by the user.

Figure 2:
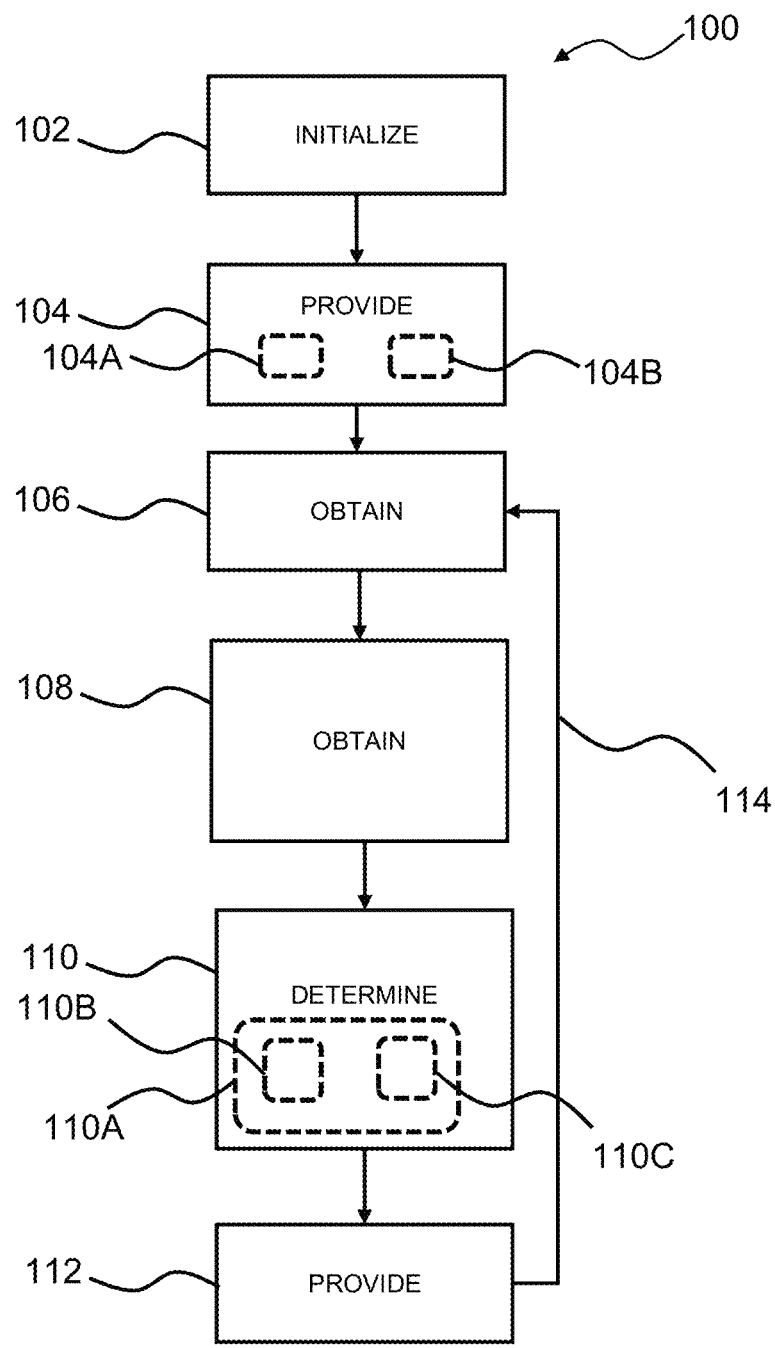
FIG. 2 is a flow diagram of an exemplary method according to the disclosure.

FIG. 2 is a flow diagram of an exemplary method for situated design of a hearing algorithm of a hearing device. The method 100, optionally performed in an accessory device, comprises initializing 102 a model comprising a parameterized objective function; providing 104 one or more operating parameters indicative of the hearing algorithm to the hearing device, the one or more operating parameters optionally including a hearing algorithm identifier and/or a set of hearing device parameters; obtaining 106 operating data comprising corresponding input data x(t) and output data y(t) of the hearing device; obtaining 108 evaluation data r(t) indicative of user evaluation of the output data; determining 110 one or more updated operating parameters based on the model, the operating data and the evaluation data; and providing 112 the updated operating parameters to the hearing device. The method returns 114 to obtaining 106 operating data.

In one or more exemplary methods, providing 104 one or more operating parameters to the hearing device comprises providing 104A a hearing algorithm f or a hearing algorithm identifier to the hearing device. In other words, the agent 8 may be able to select which hearing algorithm, e.g. from a set of a plurality of hearing algorithms, the hearing device 6 should apply.

In one or more exemplary methods, providing 104 one or more operating parameters to the hearing device comprises providing 104B one or more hearing device parameters θ to the hearing device.

In the method 100, the model is a generative probabilistic model m given by p(x, y, r, f, θ, z|m), where x is input data of the hearing device, y is output data of the hearing device, r is evaluation data, f is a hearing algorithm identifier, θ is hearing device parameters, and z is latent variables and the hearing algorithm is a dynamical system given by $s_{t+1} = f(s_t, x_t, \theta)$ $y_t = g(s_t)$ where t is the time index; $x_t$ is input data, $s_t$ is a state vector, $y_t$ is output data which is a fixed function g(·) of the states $s_t$, f(·) denotes the hearing algorithm and θ comprises a set of hearing device parameters.

In one or more exemplary methods, determining 110 one or more updated operating parameters comprises solving 110A a probabilistic inference problem, e.g. given by $p(f, \theta | d_{\leq t} = \{(x, y, r)_{\leq t}\}, r_{> t} > 0, m)$, where f is a hearing algorithm, θ is hearing device parameters, $d_{\leq t} = \{(x, y, r)_{\leq t}\}$ is a first constraint respecting past observations, and $r_{> t} > 0$ is a second constraint that future evaluation data should be indicative of a positive user evaluation of the output data. Solving 110A the probabilistic inference problem comprises implementing 110B message passing on a factor graph realization, e.g. a Forney-style Factor graph of the model.

In one or more exemplary methods, wherein determining 110 one or more updated operating parameters based on the model, the operating data and the evaluation data comprises minimizing 110C a function, wherein the function is an alpha-divergence function, such as a function F given by:

$$F[q] = \sum_z q(z) \log \frac{q(z)}{p(d, z)},$$

where the function F is a function of the variational distribution q(z) and d are data tuples (x, y, r). It is to be understood that other divergence functions may be employed.

Figure 3:
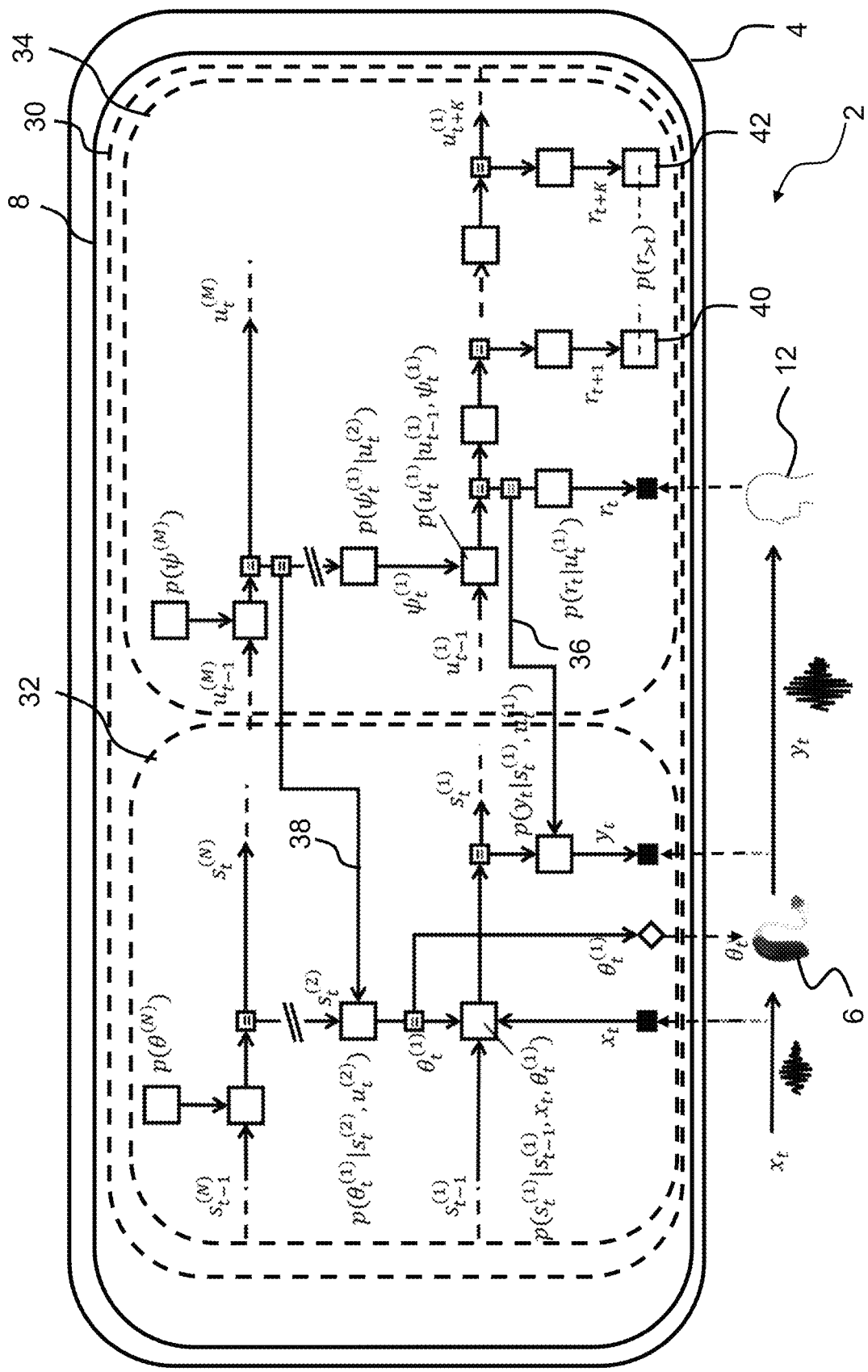
FIG. 3 illustrates an exemplary implementation of the model in an agent of an accessory device.

FIG. 3 illustrates an exemplary implementation of the model in an agent 8. In general, the agent may be implemented as an application or software module installed in the memory of an accessory device, such as a smartphone, smartwatch, or tablet computer.

The structure of the model 30 of the agent 8 is shown inside the accessory device 4. The model 30 comprises a first model 32 and a second model 34, wherein the first model 32 is a generative probabilistic model for the input data x(t) and the output data y(t) and the second model 34 is a generative probabilistic model for the evaluation data r(t). Thus, the first model 32 is a generative probabilistic model for hearing device input (input data) and output (output data) signals $\{\forall_t:(x_t, y_t)\}$. The second model 34 is a generative probabilistic model for user responses $\{\forall_t:r_t\}$. The lines 36, 38 connect states in the second model 34 (user model) to factors in the first model 32. Taken together, the agent's model 30 is a generative probabilistic model for the "sensory" inputs of the agent, i.e., for $\{d_t=(x_t, y_t, r_t):t=1, 2, \ldots\}$.

The agent iteratively determines the optimal tuning parameter settings or operating parameters (θ) for a given hearing algorithm f. The task to find the best hearing algorithm f from a candidate set of algorithms $\{f_k:k=1, \ldots K\}$ is similar to the parameter estimation problem. The first model 32 is a (probabilistic) model of the hearing device signal processing algorithm. Usually, the model for the signal processing algorithm will be a dynamical hierarchical structure. A typical example for the bottom layer is given by $$p(s_t^{(1)}|s_{t-1}^{(1)}, x_t, \theta_t^{(1)}) = N(s_t^{(1)}|f(s_{t-1}^{(1)}, x_t, \theta_t^{(1)}), \Sigma_s) \quad (6)$$

$$p(y_t|s_t^{(1)}(\text{end}), u_t^{(1)}) = N(y_t|g(s_t^{(1)}), \sigma_y^2(u_t^{(1)})),$$

where $s_t^{(n)}$ is the internal state vector at the n-th layer. This is basically the hearing algorithm of equation 3 with some Gaussian noises at relevant places to create room (uncertainties) for inferring the preferred user settings. What is unusual about equation 6, is that the observation variance $\sigma_y^2$ is a function of $u_t^{(1)}$ from the second model 34, which, as will be seen later, reflects the (belief about) the end user's evaluation of the current hearing device behavior.

The tuning parameters $\theta_t^{(1)}$ are also considered to be subject to a dynamical system of the form $$p(s_t^{(2)}|s_{t-2}^{(2)}, \theta_t^{(2)}) \quad (7)$$

$$p(\theta_t^{(1)}|s_t^{(2)}, u_t^2)$$

In this system, $s_t^{(2)}$ are (hidden) state variables of the second layer and $\theta_t^{(1)}$ is modeled as an 'observation model' that depends on the state of the superior layer ($s_t^{(2)}$) and second layer evaluation states ($u_t^{(2)}$) of the user model (first model 32). This hierarchical model for the hearing device signal processing system can be continued to higher layers. In FIG. 3, an N-layer hierarchical dynamic system is drawn for the hearing device algorithm.

The parameters $\theta_t^{(n)}$, n=1, ..., N, are also treated as hidden states in the agent's model 30. The agent 8 computes posterior distributions over these parameter states through (message passing-based) inference. At any time, the agent 8 may submit to the hearing device 6 a set of trial values $\theta_t = \hat{\theta}_t$ for the parameters, based on the agent's beliefs over $\theta_t^{(n)}$. In FIG. 3, it is shown how $\hat{\theta}_t$ is drawn from the posterior distribution over $\theta_t^{(1)}$. Submitting a set of parameter values $\hat{\theta}_t$ to the hearing device 6 is called a TRY (or an action; by the agent 8). A typical method for drawing trial values $\hat{\theta}_t$ is to draw from the posterior distribution over the parameters $\theta_t^{(n)}$. This is often referred to as Thompson Sampling.

The user may at any time cast appraisals or provide feedback $r_t$ about the current hearing device behavior, i.e. provide evaluation data. The feedback (appraisals) from the user may comprise pressing a button to indicate like/dislike or may consist of physiological signal recordings such as heart rate and EEG signals, or a combination thereof.

The agent 8 considers these appraisals $r_t$ (also denoted evaluation data) as another (set of) observed signals. The agent 8 contains second model 34 being a generative probabilistic user model to predict these appraisals. In similar ways to the hearing device model (first model 32), the user model (second model 34) is also a hierarchical probabilistic system. The m-th layer in the user model is typically given by $$p(u_t^{(m)}|u_{t-1}^{(m)}, \psi_t^{(m)}) \quad (8a)$$

$$p(\psi_t^{(m-1)}|u_t^{(m)}) \quad (8b),$$

where equation 8a describes the user model as a (Markov) dynamic system with hidden states $u_t^{(m)}$. The transition probability between states is controlled by control variables $\psi_t^{(m)}$. According to equation 8b, these control variables are a function of the states of the superior layer. At the bottom layer (layer 1 in FIG. 3), the observations $\{\forall_t : r_t\}$ are also generated as a (probabilistic) function of the states. In the second model, the hidden states $u_t^{(m)}$ correspond to predictive causes for the evaluation data $r_t$.

Note that the second model 34 may contain some temporal thickness in the sense that future observations $r_{>t}=(r_{t+1}, r_{t+2}, \ldots)$ are part of the second model 34. The second model 34 optionally allows to set prior expectations $p(r_{>t})$ on future observations, as indicated in FIG. 3 by the nodes 40, 42 that terminate the edges corresponding to $r_{>t}$. These prior expectations for future observations constrain the inference in the model to take into account that future observations will be positively valued. By including these prior constraints, any inference for actions will take into account that future appraisals are expected to be positively valued, no matter in what environment the second model is marinated.

Optionally, constraints of the model 30 are not limited to setting constraints on the future observations $r_{>t}$. Constraints may be set on future values for hidden variables such as $u_{>t}$. Note that the agent's model 30 contains links 36, 38 that directly connect variables in the hearing device signal processing model 32 with variables in the user model 34. For instance, the connection 36 connects the hidden user model state $u_t^{(1)}$ to the node $p(y_t|s_t^{(1)}, u_t^{(1)})$ in the signal processing model 32. An exemplary node function ("observation model") would be $p(y_t|s_t^{(1)}, u_t^{(1)}) = N(y_t|f(s_t^{(1)}), g(u_t^{(1)}))$. In this equation, the variance of the observation model depends on the state of the user model 34. Thus, in this model the estimated "state of satisfaction' can affect the precision of the observations $y_t$. If high user satisfaction states are associated with high precision (ie small variance) for the observed hearing device signal outputs (and vice versa, low user satisfaction states with low precision for the hearing device output signal observations), the model 30 of the agent 8 will only learn from HA behavior that is associated with high user satisfaction states. In this way, the user model provides context that modulates the learning rates for the hearing device signal processing model.

The above set of equations provide a typical example of a model 30 for a probabilistic agent 8 that designs a hearing algorithm trough interaction with end users 12. Details of actual implementations may differ.

Inference and Learning by Message Passing

The agent's model 30 specifies constraint(s) between observed variables $x_t$, $y_t$, $r_t$, (unobserved) future observations $r_{>t}$, interventional variables (actions, trials) $\theta_t$, and hidden (unobserved) state variables $s_t^{(n)}, \theta_t^{(n)}, u_t^{(m)}, \psi_t^{(m)}$. In order to simplify the notation for inference and learning, the variables are grouped at time step t into a set of observed variables $d_t=\{x_t, y_t, r_t\}$ and unobserved variables $z_t=\{s_t^{(n)}, \theta_t^{(n)}, u_t^{(m)}, \psi_t^{(m)}, \theta_t, r_{>t}\}$. Technically, tuning parameters and hyperparameters of the model 30 should be added to the set of unobserved variables ($z_t$). The agent 30 has only one goal: do Bayesian inference for the unobserved variables (including inference for its actions), given the observed variables and given the model assumptions. This is in general an intractable problem. In a Forney-style Factor Graph framework, Bayesian inference can be approximated by message passing algorithms. Examples of message passing algorithms for FFGs include belief propagation, variational message passing and expectation propagation. Variational message passing is a message passing implementation of Variational Inference. In variational inference, a so-called Free Energy Functional F is defined:

$$F[q] = \sum_z q(z) \log \frac{q(z)}{p(d,z)}$$

which is a functional of a variational distribution q(z). Minimization of the free energy F[q] with respect to q leads to approximate Bayesian inference. F can be minimized by message passing in an FFG. Thus, by applying message passing-based inference in an FFG of the probabilistic model e.g. as specified in FIG. 3, the agent 8 will design a hearing algorithm that optimizes expected future user satisfaction rates in turn providing an improved hearing algorithm.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

It may be appreciated that FIGS. 1-3 comprise some modules or operations which are illustrated with a solid line and some modules or operations which are illustrated with a dashed line. The modules or operations which are comprised in a solid line are modules or operations which are comprised in the broadest example embodiment. The modules or operations which are comprised in a dashed line are example embodiments which may be comprised in, or a part of, or are further modules or operations which may be taken in addition to the modules or operations of the solid line example embodiments. It should be appreciated that these operations need not be performed in order presented. Furthermore, it should be appreciated that not all of the operations need to be performed. The exemplary operations may be performed in any order and in any combination.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary embodiments may be implemented at least in part by means of both hardware and software, and that several "means", "units" or "devices" may be represented by the same item of hardware.

The various exemplary methods, devices, agents, and systems described herein are described in the general context of method steps processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform specified tasks or implement specific abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 2 hearing system
4 accessory device, smartphone
6 hearing device
8 agent
10 external device
12 user
14 receiving model
18 TRY
20 EXECUTE
22 EVALUATE
24 ADAPT
26 ASSUME
30 model
32 first model
34 second model
36 first line/link between first model and second model for provision of a first output from the second model to the first model
38 second line/link between first model and second model for provision of a second output from the second model to the first model
40 node
42 node
100 method for situated design of a hearing algorithm of a hearing device
102 initializing a model comprising a parameterized objective function
104 providing one or more operating parameters indicative of the hearing algorithm to the hearing device
104A providing a hearing algorithm f or a hearing algorithm identifier indicative off to the hearing device
104B providing one or more hearing device parameters $\theta$ to the hearing device
106 obtaining operating data comprising corresponding input data x(t) and output data y(t) of the hearing device
108 obtaining evaluation data r(t) indicative of user evaluation of the output data
110 determining one or more updated operating parameters based on the model, the operating data and the evaluation data
110A solving a probabilistic inference problem
110B implementing message passing on a factor graph realization
110C minimizing a function
112 providing the updated operating parameters to the hearing device
114 return to obtaining operating data

The invention claimed is:

1. An electronic apparatus for configuring a hearing device, comprising:
a memory;
a processing unit coupled to the memory, the processing unit configured to obtain a model comprising a parameterized objective function, and to obtain operating data comprising input data and output data associated with the hearing device;
wherein the processing unit of the electronic device is also configured to obtain evaluation data indicative of an evaluation of the output data associated with the hearing device;
wherein the processing unit of the electronic device is further configured to determine one or more updated operating parameters based on the model, the operating data, and the evaluation data;
wherein the electronic apparatus further comprises a communication interface configured to provide the updated operating parameters to the hearing device to configure the hearing device; and
wherein the processing unit is configured to determine the one or more updated operating parameters based on the model, the operating data, and the evaluation data based on an alpha-divergence function.

2. The electronic apparatus of claim 1, wherein the electronic apparatus is configured to perform a situated design of a hearing algorithm for the hearing device.

3. The electronic apparatus according to claim 1, wherein the processing unit is configured to implement message passing to determine the one or more updated operating parameters.

4. The electronic apparatus according to claim 3, wherein the processing unit is configured to implement the message passing on a factor graph.

5. The electronic apparatus according to claim 4, wherein the factor graph is based on the model.

6. The electronic apparatus according to claim 4, wherein the factor graph is a realization of the model.

7. The electronic apparatus according to claim 4, wherein the factor graph is a Forney-style Factor graph realization of the model.

8. The electronic apparatus according to claim 1, wherein the electronic apparatus is configured to provide one or more parameters associated with a hearing algorithm to the hearing device.

9. The electronic apparatus according to claim 1, wherein the model comprises a generative probabilistic model.

10. The electronic apparatus according to claim 9, wherein the generative probabilistic model is a generative probabilistic model m given by $$p(x, y, r, f, \theta, z|m),$$

where x is input data of the hearing device, y is output data of the hearing device, r is evaluation data, $f$ denotes a hearing algorithm, $\theta$ represents hearing device parameter(s), and z is latent variable(s).

11. The electronic apparatus according to claim 1, wherein the model is a hierarchical Bayesian dynamical system.

12. A method performed by an electronic apparatus to carry out a situated design process to configure a hearing device, the method comprising:
obtaining a model comprising a parameterized objective function;
electronically obtaining operating data comprising input data and output data associated with the hearing device;
electronically obtaining evaluation data indicative of an evaluation of the output data associated with the hearing device;
determining, by a processing unit that is configured to perform signal processing, one or more updated operating parameters based on the model, the operating data, and the evaluation data; and
providing the updated operating parameters to the hearing device to thereby configure the hearing device;
wherein the act of determining one or more updated operating parameters based on the model, the operating data, and the evaluation data comprises minimizing an alpha-divergence function.

13. The method according to claim 12, further comprising providing one or more operating parameters associated with a hearing algorithm to the hearing device.

14. The method according to claim 13, wherein the act of providing one or more operating parameters to the hearing device comprises providing a hearing algorithm identifier to the hearing device.

15. The method according to claim 13, wherein the act of providing one or more operating parameters to the hearing device comprises providing one or more hearing device parameters to the hearing device.

16. The method according to claim 12, wherein the model comprises a generative probabilistic model.

17. The method according to claim 16, wherein the generative probabilistic model is a generative probabilistic model m given by $$p(x, y, r, f, \theta, z|m),$$

where x is input data of the hearing device, y is output data of the hearing device, r is evaluation data, $f$ denotes a hearing algorithm, θ represents hearing device parameter(s), and z is latent variable(s).

18. The method according to claim 16, wherein the model is a hierarchical Bayesian dynamical system.

19. The method according to claim 12, wherein the situated design process is for designing a hearing algorithm for the hearing device, the hearing algorithm being a dynamical system given by $$s_{t+1} = f(s_t, x_t, \theta)$$

$$y_t = g(s_t)$$

where t is a time index; $x_t$ is input data, $s_t$ is a state vector, $y_t$ is output data which is a function $g(\cdot)$ of $s_t$, $f(\cdot)$ denotes a hearing algorithm, and θ represents hearing device parameter(s).

20. The method according to claim 12, wherein the act of determining one or more updated operating parameters comprises implementing message passing.

21. The method according to claim 20, wherein the message passing is implemented on a factor graph.

22. The method according to claim 21, wherein the factor graph is based on the model.

23. The method according to claim 21, wherein the factor graph is a realization of the model.

24. The method according to claim 21, wherein the factor graph is a Forney-style Factor graph realization of the model.

25. The method according to claim 12, wherein the alpha-divergence function is a function F given by:

$$F[q] = \sum_z q(z) \log \frac{q(z)}{p(d, z)}$$

where q(z) is a variational distribution.

26. The method according to claim 12, wherein the model comprises a first model and a second model, wherein the first model is a generative probabilistic model for the input data and the output data, wherein the second model is a generative probabilistic model for the evaluation data, and wherein the first model is based on an output of the second model.

27. An electronic apparatus configured to perform the method of claim 12.

28. The electronic apparatus of claim 27, wherein the electronic apparatus comprises an accessory device.

29. A hearing system comprising a hearing device and the electronic apparatus of claim 27.

30. A method performed by an electronic apparatus to carry out a situated design process to configure a hearing device, the method comprising:
obtaining a model comprising a parameterized objective function;
electronically obtaining operating data comprising input data and output data associated with the hearing device;
electronically obtaining evaluation data indicative of an evaluation of the output data associated with the hearing device;
determining, by a processing unit that is configured to perform signal processing, one or more updated operating parameters based on the model, the operating data, and the evaluation data; and
providing the updated operating parameters to the hearing device to thereby configure the hearing device;
wherein the act of determining one or more updated operating parameters comprises solving a probabilistic inference problem given by $$p(f, \theta, |d_{<t} = \{(x, y, r)_{<t}\}, r_{>t} > 0, m),$$

where $f$ denotes a hearing algorithm, θ represents hearing device parameter(s), $d_{<t} = \{(x, y, r)_{<t}\}$ is a first constraint associated with past observation(s), and $r_{>t} > 0$ is a second constraint associated with future evaluation data.

* * * * *